(12) United States Patent
Eisinger

(10) Patent No.: US 11,553,920 B2
(45) Date of Patent: Jan. 17, 2023

(54) TROCAR RETAINER ASSEMBLY FOR SURGICAL STAPLER

(71) Applicant: Covidien LP, Mansfield, MA (US)

(72) Inventor: Joseph Eisinger, Northford, CT (US)

(73) Assignee: Covidien LP, Mansfield, MA (US)

( * ) Notice: Subject to any disclaimer, the term of this patent is extended or adjusted under 35 U.S.C. 154(b) by 87 days.

(21) Appl. No.: 17/306,223

(22) Filed: May 3, 2021

(65) Prior Publication Data

US 2022/0346795 A1 Nov. 3, 2022

(51) Int. Cl.
*A61B 17/34* (2006.01)
*A61B 17/115* (2006.01)

(52) U.S. Cl.
CPC .......... *A61B 17/1155* (2013.01); *A61B 17/34* (2013.01); *A61B 2017/348* (2013.01)

(58) Field of Classification Search
CPC ............... A61B 17/1155; A61B 17/34; A61B 2017/348
USPC ...................... 227/175.1–182.1; 606/142–143
See application file for complete search history.

(56) References Cited

U.S. PATENT DOCUMENTS

| | | | |
|---|---|---|---|
| 3,193,165 | A | 7/1965 | Akhalaya et al. |
| 3,388,847 | A | 6/1968 | Kasulin et al. |
| 3,552,626 | A | 1/1971 | Astafiev et al. |
| 3,638,652 | A | 2/1972 | Kelley |
| 3,771,526 | A | 11/1973 | Rudie |
| 4,198,982 | A | 4/1980 | Fortner et al. |
| 4,207,898 | A | 6/1980 | Becht |
| 4,289,133 | A | 9/1981 | Rothfuss |
| 4,304,236 | A | 12/1981 | Conta et al. |
| 4,319,576 | A | 3/1982 | Rothfuss |
| 4,350,160 | A | 9/1982 | Kolesov et al. |
| 4,351,466 | A | 9/1982 | Noiles |
| 4,379,457 | A | 4/1983 | Gravener et al. |
| 4,473,077 | A | 9/1984 | Noiles et al. |

(Continued)

FOREIGN PATENT DOCUMENTS

| | | | | |
|---|---|---|---|---|
| AU | 2014216027 | A1 * | 4/2015 | ........... A61F 2/0063 |
| CA | 908529 | A | 8/1972 | |

(Continued)

OTHER PUBLICATIONS

Written Opinion dated Jul. 29, 2022 issued in corresponding PCT Appln. No. PCT/IB2022/053861.

*Primary Examiner* — Robert F Long
(74) *Attorney, Agent, or Firm* — Carter, DeLuca & Farrell LLP

(57) ABSTRACT

An end effector including an elongate shaft with a lumen has an adapter at one end for coupling with a handle assembly of a surgical instrument. A support member has opposed openings defining a passage. The support member is positionable within the lumen. A trocar assembly has a sleeve and a trocar member. The trocar assembly is insertable into the passage. The sleeve includes an orifice extending through a wall of the sleeve. A pin is disposed in the elongate shaft and is slidable in a direction that is transverse to a longitudinal axis of the elongate shaft. The pin is insertable into the orifice for retaining the trocar assembly longitudinally stationary relative to the elongate shaft that defines an inserted position of the pin. The support member includes a proximal ramp that is engageable with a head of the pin to maintain the pin in the orifice of the sleeve.

20 Claims, 9 Drawing Sheets

(56) References Cited

U.S. PATENT DOCUMENTS

| | | |
|---|---|---|
| 4,476,863 A | 10/1984 | Kanshln et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |

(56) References Cited

U.S. PATENT DOCUMENTS

| | | |
|---|---|---|
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,673,088 B1 * | 1/2004 | Vargas .................. A61B 17/11 606/185 |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |

(56) References Cited

U.S. PATENT DOCUMENTS

| | | |
|---|---|---|
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,141,763 B2 * | 3/2012 | Milliman ............ A61B 17/115 227/181.1 |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,348,122 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,806,973 B2 | 8/2014 | Ross et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |
| 9,351,729 B2 | 5/2016 | Orban, III et al. |
| 9,351,731 B2 | 5/2016 | Carter et al. |

(56) References Cited

U.S. PATENT DOCUMENTS

| | | |
|---|---|---|
| 9,364,229 B2 | 6/2016 | D'Agostino et al. |
| 9,370,366 B2 | 6/2016 | Mozdzierz |
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,617,422 B2 | 4/2020 | Guerrera et al. |
| 10,624,646 B2 | 4/2020 | Bae et al. |
| 10,639,041 B2 | 5/2020 | Williams |
| 10,653,414 B2 | 5/2020 | Williams |
| 10,675,050 B2 * | 6/2020 | Staunton .............. A61B 50/13 |
| 10,898,196 B2 | 1/2021 | Sapienza et al. |
| 11,350,939 B2 * | 6/2022 | Sgroi, Jr. ........... A61B 17/3462 |
| 2003/0111507 A1 | 6/2003 | Nunez |
| 2005/0023325 A1 * | 2/2005 | Gresham .............. A61B 17/115 |
| | | 227/176.1 |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0097025 A1 * | 5/2006 | Milliman .............. A61B 17/115 |
| | | 227/175.1 |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0108741 A1 * | 5/2010 | Hessler ................. A61B 17/115 |
| | | 227/179.1 |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0132964 A1 * | 6/2011 | Weisenburgh, II .......................... A61B 17/3209 |
| | | 227/176.1 |
| 2011/0144640 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105546 A1 * | 5/2013 | Milliman ........... A61B 17/0482 |
| | | 227/175.1 |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |
| 2013/0200131 A1 | 8/2013 | Racenet et al. |
| 2013/0206816 A1 | 8/2013 | Penna |

(56) References Cited

U.S. PATENT DOCUMENTS

| | | |
|---|---|---|
| 2013/0240597 A1 | 9/2013 | Milliman et al. |
| 2013/0277411 A1 | 10/2013 | Hodgkinson et al. |
| 2013/0284792 A1 | 10/2013 | Ma |
| 2013/0292449 A1 * | 11/2013 | Bettuchi ............. A61B 17/1152 227/175.1 |
| 2014/0008413 A1 | 1/2014 | Williams |
| 2014/0046352 A1 | 2/2014 | Reboa et al. |
| 2014/0158747 A1 | 6/2014 | Measamer et al. |
| 2014/0284370 A1 | 9/2014 | Sahin |
| 2015/0014392 A1 * | 1/2015 | Williams ............. A61B 17/072 227/180.1 |
| 2015/0083772 A1 | 3/2015 | Miller et al. |
| 2015/0173763 A1 | 6/2015 | Liu |
| 2015/0209045 A1 | 7/2015 | Hodgkinson et al. |
| 2015/0351769 A1 * | 12/2015 | Lee .................... A61B 17/1155 227/179.1 |
| 2015/0374371 A1 * | 12/2015 | Richard ........... A61B 17/07207 227/176.1 |
| 2017/0105736 A1 * | 4/2017 | Chen ................ A61B 17/1155 |
| 2021/0000500 A1 * | 1/2021 | Sgroi, Jr. ........... A61B 17/3421 |
| 2021/0315663 A1 * | 10/2021 | Williams ............... A61B 90/70 |
| 2022/0047260 A1 * | 2/2022 | Eisinger ............ A61B 17/1155 |

FOREIGN PATENT DOCUMENTS

| | | | | |
|---|---|---|---|---|
| CA | 2805365 A1 | 8/2013 | | |
| CA | 3080947 A1 * | 1/2021 | ......... | A61B 17/1155 |
| CN | 104039244 A | 9/2014 | | |
| CN | 104042288 A | 9/2014 | | |
| CN | 104367360 A | 2/2015 | | |
| DE | 1057729 B | 5/1959 | | |
| DE | 3301713 A1 | 7/1984 | | |
| EP | 0152382 A2 | 8/1985 | | |
| EP | 0173451 A1 | 3/1986 | | |
| EP | 0190022 A2 | 8/1986 | | |
| EP | 0282157 A1 | 9/1988 | | |
| EP | 0503689 A2 | 9/1992 | | |
| EP | 1354560 A2 | 10/2003 | | |
| EP | 2138118 A2 | 12/2009 | | |
| EP | 2168510 A1 | 3/2010 | | |
| EP | 2238926 A2 | 10/2010 | | |
| EP | 2524656 A2 | 11/2012 | | |
| EP | 3078335 A1 * | 10/2016 | ......... | A61B 17/1155 |
| FR | 1136020 A | 5/1957 | | |
| FR | 1461464 A | 2/1966 | | |
| FR | 1588250 A | 4/1970 | | |
| FR | 2443239 A1 | 7/1980 | | |
| GB | 1185292 A | 3/1970 | | |
| GB | 2016991 A | 9/1979 | | |
| GB | 2070499 A | 9/1981 | | |
| JP | 2004147969 A | 5/2004 | | |
| JP | 2013138860 A | 7/2013 | | |
| NL | 7711347 A | 4/1979 | | |
| SU | 1509052 A1 | 9/1989 | | |
| WO | 8706448 A1 | 11/1987 | | |
| WO | 8900406 A1 | 1/1989 | | |
| WO | 9006085 A1 | 6/1990 | | |
| WO | WO-9805261 A2 * | 2/1998 | ......... | A61B 17/1622 |
| WO | 98/35614 A1 | 8/1998 | | |
| WO | 0154594 A1 | 8/2001 | | |
| WO | 02080781 A2 | 10/2002 | | |
| WO | 2008107918 A1 | 9/2008 | | |

* cited by examiner

TROCAR RETAINER ASSEMBLY FOR SURGICAL STAPLER

FIELD

The present disclosure generally relates to surgical instruments having trocar assemblies. In particular, the present disclosure relates to a trocar retainer assembly for a surgical stapler.

BACKGROUND

Anastomosis is the surgical joining of separate hollow organ sections. Typically, an anastomosis procedure follows surgery in which a diseased or defective section of hollow tissue is removed, and the end sections are stapled via a surgical stapler. Depending on the desired anastomosis procedure, the end sections may be joined by circular or side-to-side organ reconstruction methods, for instance.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Typically, these instruments include an elongated body portion having a handle portion at a proximal end to actuate the instrument and a staple holding component disposed at a distal end. An anvil assembly including an anvil retention rod with an attached anvil head is mounted to a trocar assembly at the distal end of the instrument adjacent the staple-holding component. Opposed end portions of tissue of the hollow organ(s) to be stapled are clamped between the anvil head and the staple holding component. The clamped tissue is stapled by driving one or more staples from the staple holding component so that the ends of the staples pass through the tissue and are deformed by the anvil head. An annular knife is advanced to core tissue within the hollow organ to free a tubular passage within the organ.

Besides anastomosis of hollow organs, surgical stapling instruments for performing circular anastomosis have been used to treat internal hemorrhoids in the rectum. Typically, during use of a circular stapling device for hemorrhoid treatment, the anvil head and the staple holding-component of the surgical stapling instrument are inserted through the anus and into the rectum with the anvil head and the staple-holding component in an open or unapproximated position. Thereafter, a pursestring suture is used to pull the internal hemorrhoidal tissue towards the anvil rod. Next, the anvil head and staple-holding component are approximated to clamp the hemorrhoidal tissue between the anvil head and the staple holding component. During the approximation of the anvil head and the staple-holding component, the trocar assembly engages the anvil retention rod. The surgical stapling instrument is fired to remove the hemorrhoidal tissue and staple the cut tissue.

SUMMARY

In an aspect of the present disclosure, an end effector includes an elongate shaft having a lumen. An adapter is disposed at a proximal end of the elongate shaft and is configured to couple the elongate shaft with a handle assembly of a surgical instrument. A support member has proximal and distal openings defining a passage therethrough. The support member is disposed in the lumen of the elongate shaft. A trocar assembly with a sleeve and a trocar member is disposed in the lumen of the elongate shaft. The trocar assembly is insertable into the passage of the support member. The sleeve includes an orifice extending through a wall of the sleeve. A pin is disposed in the elongate shaft and is slidable in a direction transverse to a longitudinal axis of the elongate shaft. The pin is insertable into the orifice of the sleeve for retaining the trocar assembly longitudinally stationary relative to the elongate shaft and defining an inserted position of the pin. A ramp is located in a proximal region of the support member and is engageable with a head of the pin to maintain the pin in the orifice of the sleeve.

In an aspect of the present disclosure, the support member is slidable relative to the elongate shaft between a proximal position and a distal position.

In aspects of the present disclosure, the support member includes first and second portions that are attachable to each other.

In another aspect of the present disclosure, the distal position of the support member relative to the elongate shaft allows movement of the pin between the inserted position and a retracted position.

In a further aspect of the present disclosure, the proximal position of the support member maintains the pin in the inserted position.

In yet another of the present disclosure, the support member further includes first and second pads that are configured to support first and second drive members to limit radial movement of the first and second drive members during an actuation sequence.

In another aspect of the present disclosure, a seal is positioned at a distal end of the support member. The seal is threadably coupled to the elongate shaft to maintain the support member in the proximal position.

In one aspect of the present disclosure, the ramp includes a tapered leading edge adapted to cammingly engage the head of the pin.

In aspects of the present disclosure, the trocar assembly is longitudinally repositionable relative to the elongate shaft with the pin in the retracted position.

According to another aspect of the present disclosure, an end effector for use with a surgical instrument includes an elongate shaft having a lumen. An adapter is disposed at a proximal end of the elongate shaft. The adapter is configured for coupling the elongate shaft with a handle assembly of the surgical instrument. A support member has proximal and distal openings defining a passage therethrough. The support member is disposed in the lumen of the elongate shaft and slidable relative to the elongate shaft between a proximal position and a distal position. A trocar assembly is insertable into the passage of the support member. The trocar assembly has a trocar member extending from a sleeve. The sleeve includes an orifice extending through a wall of the sleeve. A pin is disposed in the elongate shaft and is slidable in a direction transverse to a longitudinal axis of the elongate shaft. The pin is insertable into the orifice of the sleeve for retaining the trocar assembly longitudinally stationary relative to the elongate shaft and defining an inserted position of the pin. A ramp has a tapered edge and is located in a proximal region of the support member. The ramp is engageable with a head of the pin to maintain the pin in the orifice of the sleeve.

In aspects of the present disclosure, the support member includes first and second portions that are attachable to each other.

In another aspect of the present disclosure, the distal position of the support member relative to the elongate shaft allows movement of the pin between the inserted position and a retracted position.

In one aspect of the present disclosure, the proximal position of the support member maintains the pin in the inserted position.

In a further aspect of the present disclosure, the support member further includes first and second pads that are configured to support first and second drive members to limit radial movement of the first and second drive members during an actuation sequence.

In yet another aspect of the present disclosure, a seal is positioned at a distal end of the support member. The seal being threadably coupled to the elongate shaft to maintain the support member in the proximal position.

In aspects of the present disclosure, the tapered edge is adapted to cammingly engage the head of the pin.

In a further aspect of the present disclosure a method of coupling a trocar assembly to an end effector includes inserting a trocar assembly into a lumen of an elongate shaft. The elongate shaft has an adapter disposed at a proximal end thereof that is configured to couple the elongate shaft with a handle assembly of a surgical instrument. The method includes sliding a support member disposed in the lumen of the elongate shaft proximally thereby moving from the support member from a distal position towards a proximal position. The method includes engaging a head of a pin disposed in the elongate shaft with a ramp located in a proximal region of the support member and urging the pin into engagement with an orifice of a sleeve of the trocar assembly thereby retaining the trocar assembly longitudinally stationary with respect to the elongate shaft.

In an aspect of the present disclosure, sliding the support member includes the support member having first and second portions that are attachable to each other.

In a further aspect of the present disclosure, sliding the support member includes the support member having first and second pads that are configured to support first and second drive members to limit radial movement of the first and second drive members during an actuation sequence.

In yet another aspect of the present disclosure, engaging the head of the pin includes engaging the head of the pin with a tapered edge of the ramp.

Other features of the disclosure will be appreciated from the following description.

DESCRIPTION OF THE DRAWINGS

The accompanying drawings, which are incorporated in and constitute a part of this specification, illustrate aspects and features of the disclosure and, together with the detailed description below, serve to further explain the disclosure, in which.

DETAILED DESCRIPTION

Figure 1:
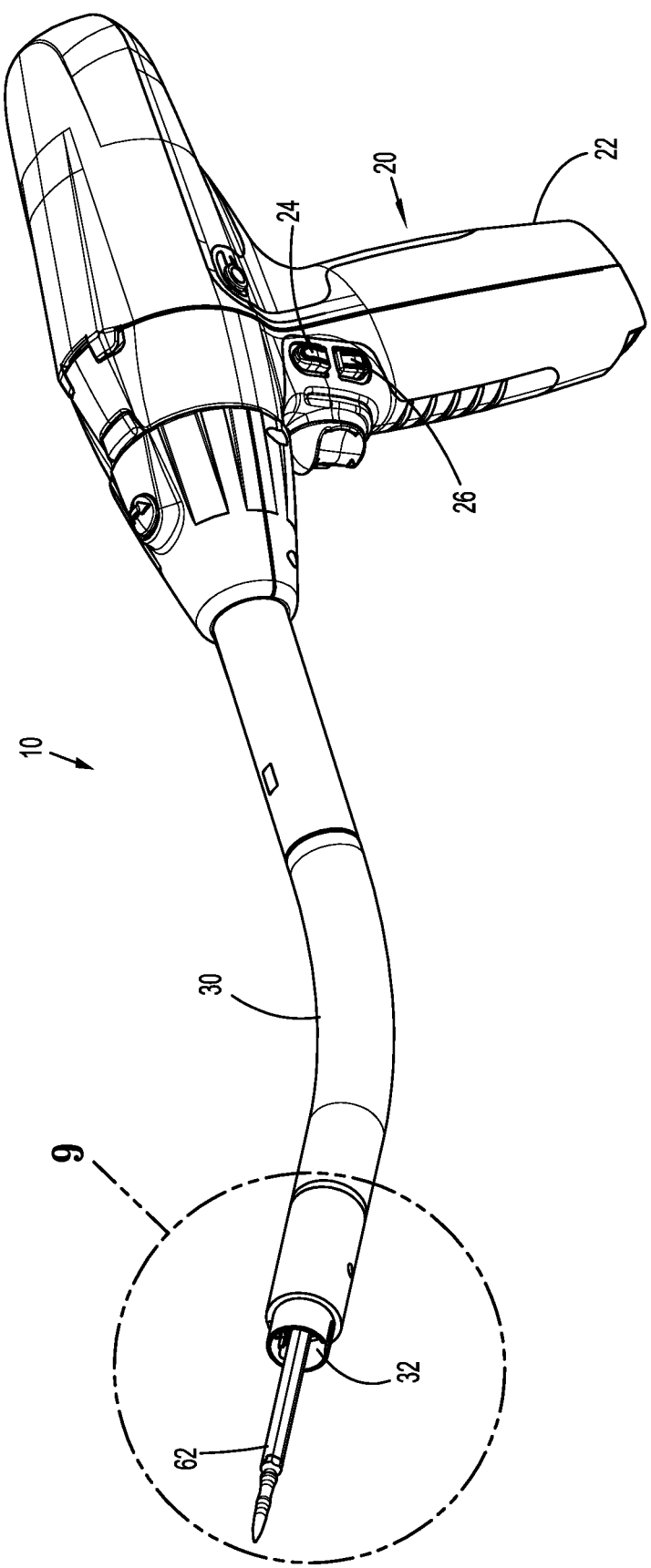
FIG. 1 is a perspective view of a surgical stapler according to an aspect of the present disclosure.

Aspects of the disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Descriptions of technical features of an aspect of the disclosure should typically be considered as available and applicable to other similar features of another aspect of the disclosure. Accordingly, technical features described herein according to one aspect of the disclosure may be applicable to other aspects of the disclosure, and thus duplicative descriptions may be omitted herein. Like reference numerals may refer to like elements throughout the specification and drawings.

Figure 2:
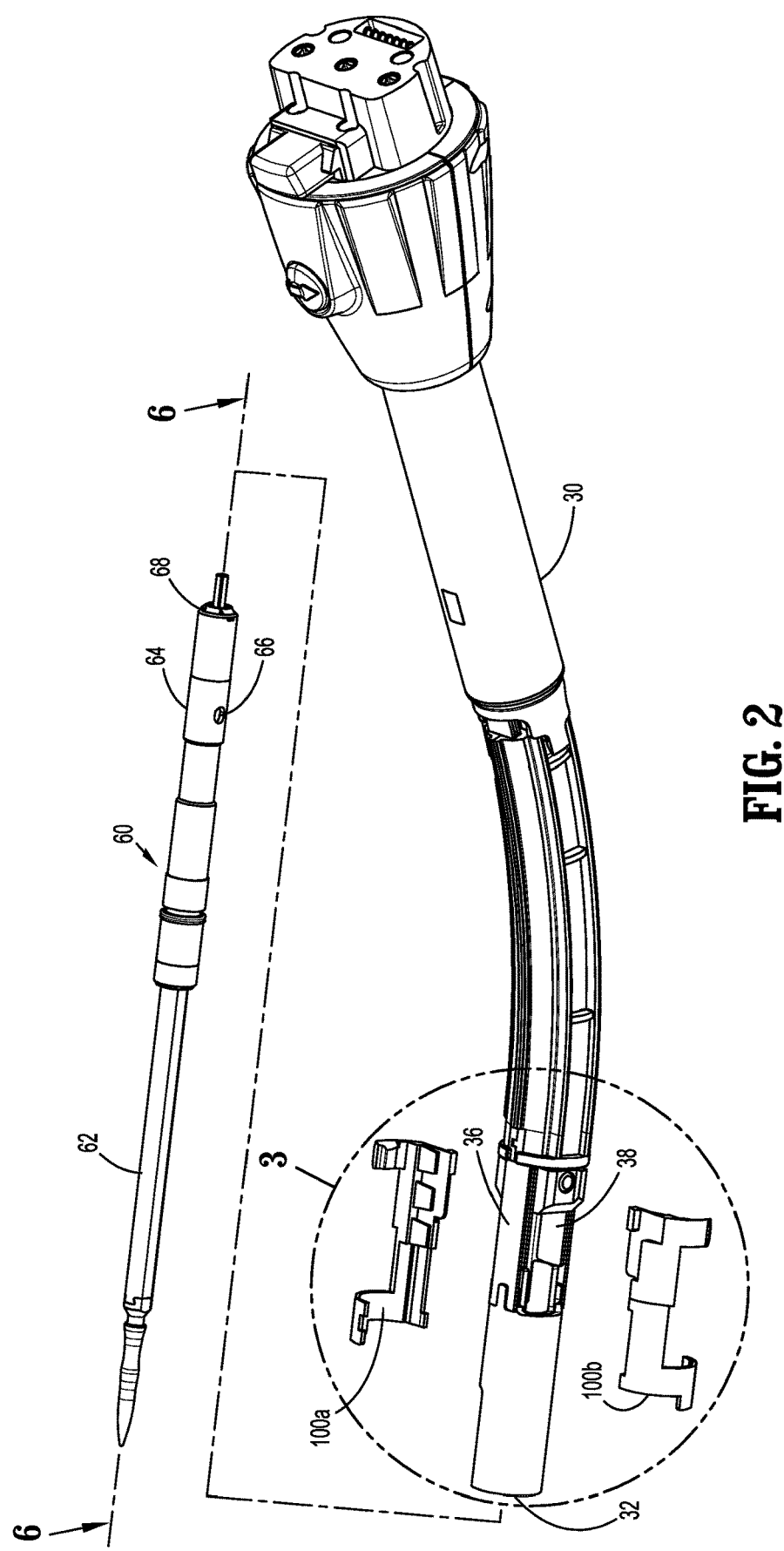
FIG. 2 is a perspective view of a tubular shaft of the surgical stapler of FIG. 1 with a trocar assembly separated from the tubular shaft and an outer wall removed from a distal portion of the tubular shaft.

Initially, with reference to FIGS. 1 and 2, a surgical stapler is shown and referenced generally as surgical stapler 10. The surgical stapler 10 is a circular stapler and includes a handle 20 assembly at one end and an elongate tubular shaft 30 extending from the handle assembly 20. The tubular shaft 30 includes an open distal end 32 for receiving a trocar assembly 60 therethrough such that the trocar assembly 60 is received in a lumen 34 (FIG. 7) of the tubular shaft 30. Although illustrated as a powered surgical stapler, the surgical stapler 10 may be a manually operated instrument such as that shown in commonly owned U.S. Pat. No. 8,348,122, the content of which is hereby incorporated herein in its entirety. The handle assembly 20 includes a power source (not shown) and buttons for operating the surgical stapler 10. A distal end of the tubular shaft 30 is adapted for coupling with a staple cartridge. A proximal end of the tubular shaft 30 includes an adapter configured for coupling the tubular shaft 30 with the handle assembly 20. The handle assembly 20 includes a fixed handle 22, an actuation button 24, and an approximation mechanism 26 for moving the trocar assembly 60 axially with respect to the tubular shaft 30. The structure and function of handle assembly 20 will only be described herein to the extent necessary. Commonly owned U.S. Pat. No. 8,806,973, the content of which is incorporated by reference herein in its entirety, discloses a surgical device having a powered actuator assembly including first and second drive members. In addition, it is envisioned that the independent actuation strokes may be completed by the same drive member completing two strokes or by two separate drive members. A support member 100 (FIG. 4), as will be described in further detail hereinbelow, is positioned in the tubular shaft 30. The trocar assembly 60 includes a trocar member 62 extending from a sleeve 64.

With continued reference to FIG. 2, a distal portion of the tubular shaft 30 is shown with an outer wall of the tubular shaft 30 removed and illustrates the location of the support member 100 (FIG. 4) relative to the tubular shaft 30. The support member 100 includes a first portion 100a and a second portion 100b. As shown, a proximal end 68 of the trocar assembly 60 is insertable through the open distal end 32 of the tubular shaft 30. With the outer wall removed, a staple band 36 and a knife band 38 are visible. The staple band 36 is operatively coupled with a staple actuator (not shown) and the knife band 38 is operatively coupled with a knife member (not shown). During a firing sequence, actuation (i.e., axial displacement) of the staple band 36 causes concomitant axial displacement of the staple actuator (not shown) thereby firing staples from the surgical stapler 10. Axial displacement of the knife band 38 causes concomitant axial displacement of a knife member (not show) for severing tissue. An example of a surgical stapling instrument with a staple band and a knife band is disclosed in commonly owned U.S. Pat. No. 10,617,422, the entire content of which is hereby incorporated by reference.

Figure 3:
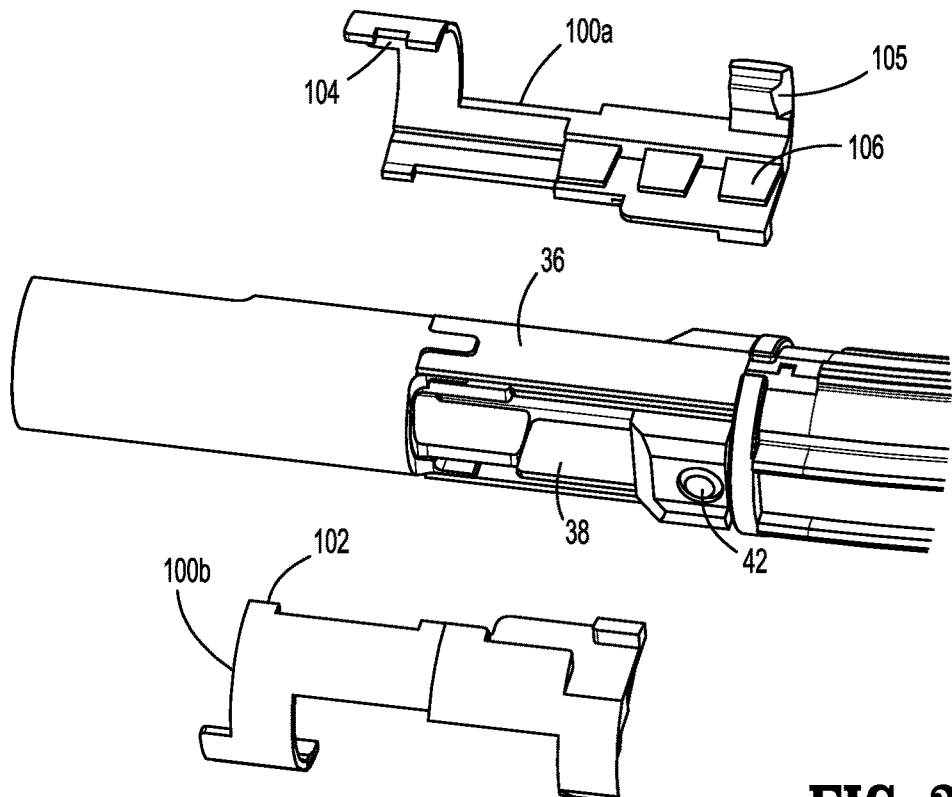
FIG. 3 is an enlarged view of the area of detail shown in FIG. 2.
Figure 4:
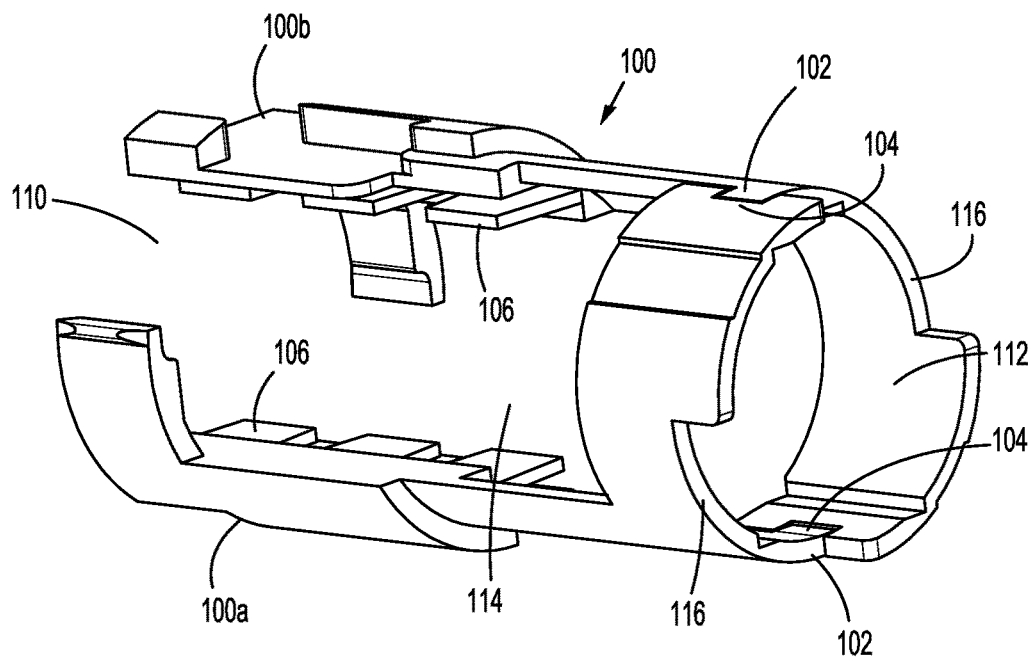
FIG. 4 is a perspective view of a band support of the trocar assembly shown in FIGS. 2 and 3.

Referring now to FIGS. 3 and 4, a more detailed explanation of the support member 100 follows. Initially, the support member 100 is formed from the first portion 100a and the second portion 100b. The support member 100 may also be a single, unitary structure. The first and second portions 100a, 100b of the support member 100 are mirror images of each other. Each of the first and second portions 100a, 100b has a tab 102 and a recess 104 located in a distal region thereof. The tabs 102 and the recesses 104 are oriented 180° apart such that the tab 102 of the first portion 100a is receivable in the recess 104 of the second portion 100b and the tab 102 of the second portion 100b is receivable in the recess 104 of the first portion 100a. The engagement between the tabs 102 and the recesses 104 is a friction fit that helps hold the first and second portions 100a, 100b together and also aligns the first portion 100a relative to the second portion 100b. Further, each of the first and second portions 100a, 100b of the support member 100 includes projections 106 that extend radially inward from an inner surface of the respective first and second portions 100a, 100b. Each projection 106 is a planar structure for separating and supporting the knife band 38 from the staple band 36. The projections 106 also limit radial deflection of the knife band 38 and the staple band 36 during actuation of the knife band 38 and the staple band 36 as will be discussed in detail hereinbelow. Additionally, proximal regions of the first and second portions 100a, 100b are configured to engage pins 40 (FIG. 14) that are slidably coupled to the tubular shaft 30 as will be discussed in detail hereinbelow. When the first and second portions 100a, 100b are coupled together, the support member 100 has an open proximal end 110 and an open distal end 112 that define a passage 114 through the support member 100. The passage 114 is configured to receive the trocar assembly 60 therethrough (FIG. 10).

Figure 5:
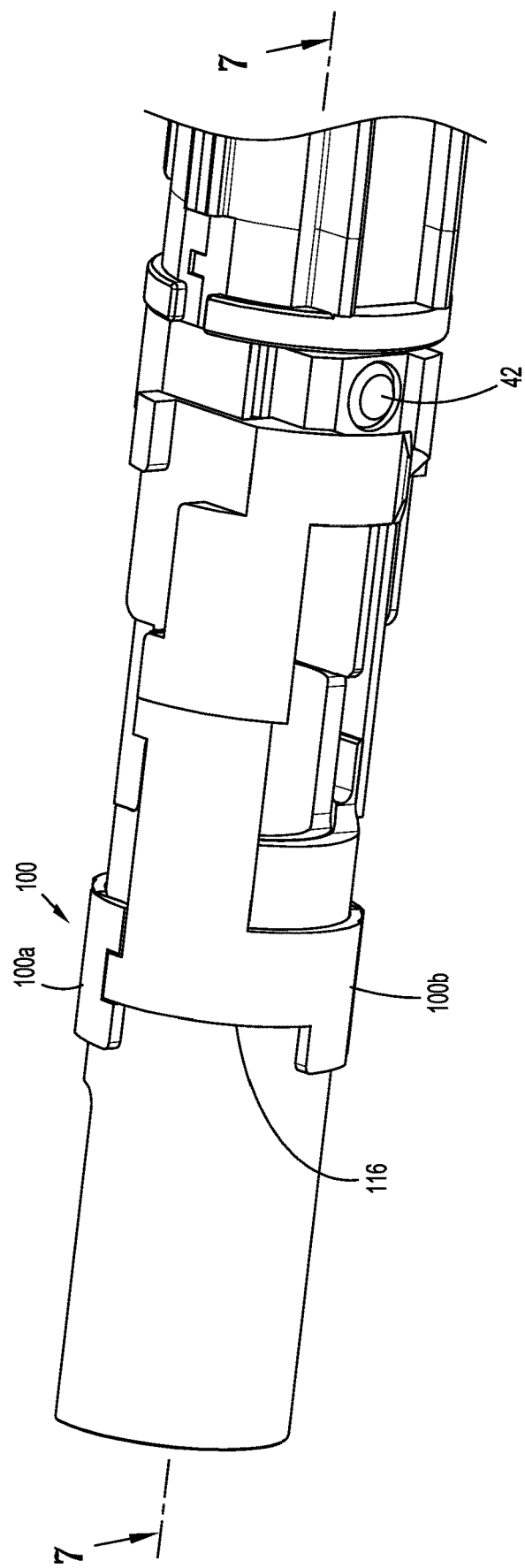
FIG. 5 is a side cut-away view of the distal portion of the tubular shaft of FIG. 2 without the trocar assembly.
Figure 6:
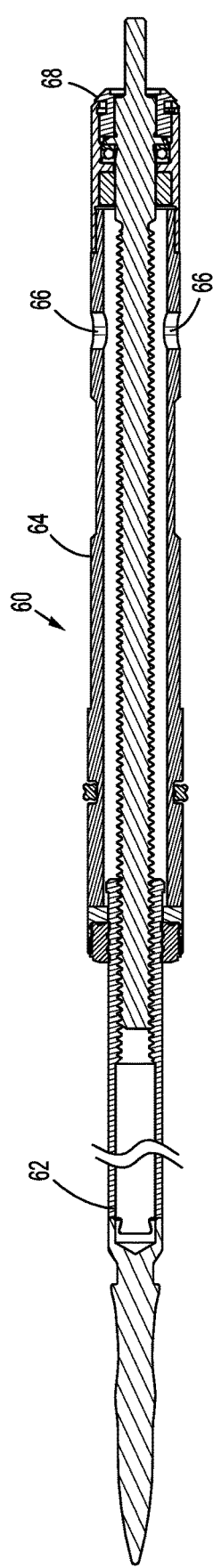
FIG. 6 is a side cross-sectional view of the trocar assembly taken along section line 6-6 of FIG. 2.
Figure 7:
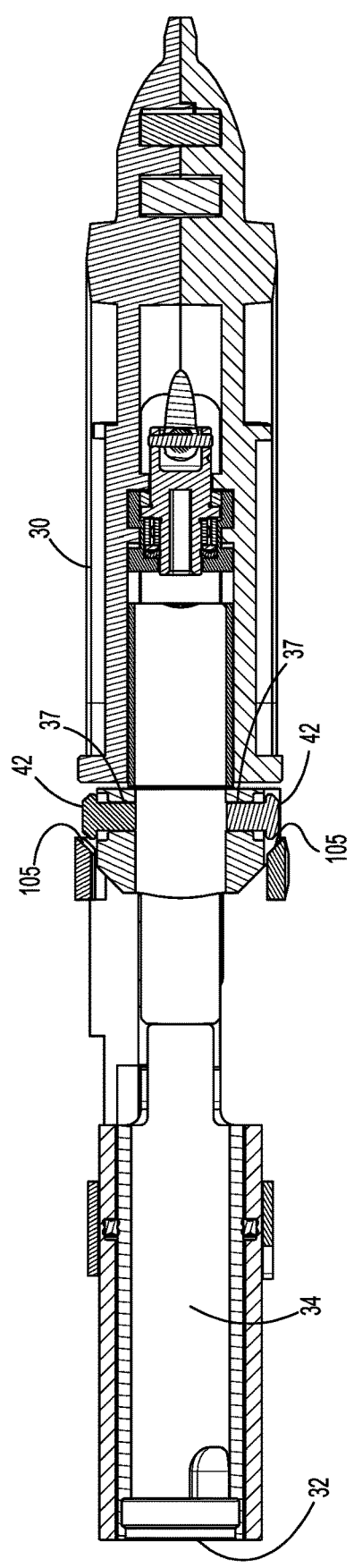
FIG. 7 is a side cross-sectional view of the trocar assembly taken along section line 7-7 of FIG. 5.
Figure 8:
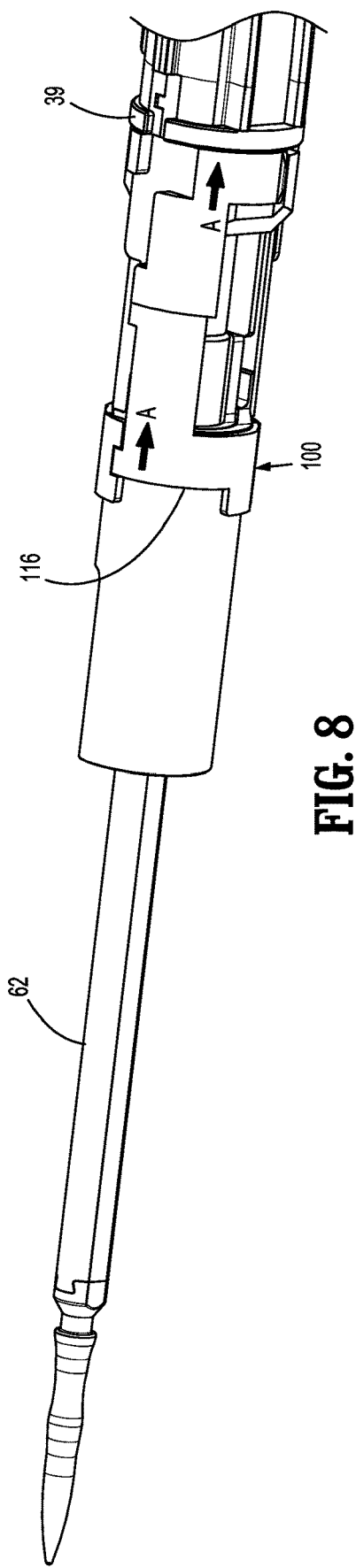
FIG. 8 is a side perspective view of the distal portion of the tubular shaft with the trocar assembly coupled thereto.

Turning now to FIGS. 5-7, the first and second portions 100a, 100b are attached to one another forming the support member 100. Regardless of whether the support member 100 is formed from the first and second portions 100a, 100b or is a unitary structure, the support member 100 is positioned circumferentially within the tubular shaft 30 such that the support member 100 and the tubular shaft 30 are coaxial. The support member 100 is slidable along a longitudinal axis of the tubular shaft 30 between a distal or first position (FIG. 5) and a proximal or second position (FIG. 8). The first position is distal relative to the second position. While the support member 100 is axially repositionable along the tubular shaft 30, the engagement between the projections 106 of the first and second portions 100a, 100b with the knife band 38 and the staple band 36 maintain the support member 100 rotationally stationary with respect to the tubular shaft 30. As shown in FIG. 7, proximal portions of the first and second portions 100a, 100b of the support member 100 have ramps or tapered cam surfaces 105 positioned at a trailing end of the support member 100. The tapered cam surfaces 105 engage heads 42 of the pins 40 that are located in the tubular shaft 30. During proximal motion of the support member 100, the engagement between the cam surfaces 105 and the heads 42 of the pins 40 urges the pins 40 to travel in receptacles 37 of the tubular shaft 30 in a direction that is orthogonal to the longitudinal axis of the tubular shaft 30. Each pin 40 has a shank 44 extending from its head 42 that moves within its respective receptacle 37 and is receivable in an orifice 66 of the sleeve 64 of the trocar assembly 60 as will be discussed in detail below. With the support member 100 in the first position, the pins 40 are freely slidable in their receptacles 37. Once the support member 100 is slid into the second position, as indicated by arrows A in FIG. 8, the cam surfaces 105 of the support member 100 urge the pins 40 toward a centerline of the tubular shaft 30 (FIG. 10). In the second position, the cam surfaces 105 of the support member 100 maintain contact with the heads 42 of the pins 40 thereby retaining the pins 40 stationary within their receptacles 37. This arrangement maintains the axial and radial position of the trocar assembly 60 with respect to the tubular shaft 30.

Figure 9:
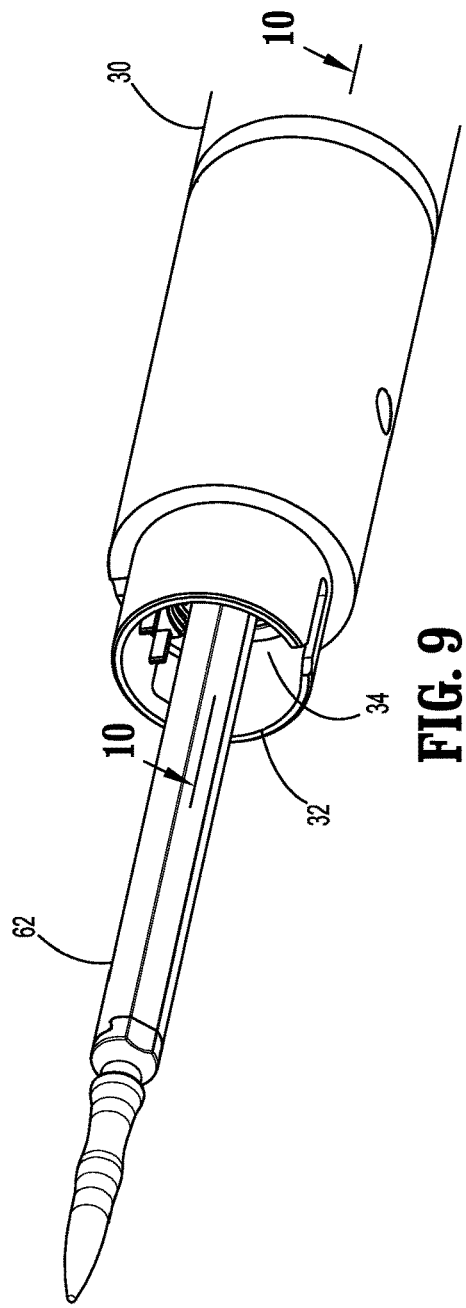
FIG. 9 is an end perspective view of the distal portion of the tubular shaft showing the trocar assembly extending therefrom.

Referring now to FIGS. 8 and 9, the trocar assembly 60 is inserted through the open distal end 32 of the tubular shaft 30 and into the lumen 34 of the tubular shaft 30. With the trocar assembly 60 positioned in the lumen 34 of the tubular shaft 30, the support member 100 is slid proximally thereby camming the pins 40 as discussed previously with respect to FIG. 7. Proximal movement of the support member 100 relative to the tubular shaft 30, as indicated by arrows A, is limited by the engagement of a proximal end of the support member 100 contacting a raised rib 39 on the tubular shaft 30, which acts as a travel limit stop.

Figure 10:
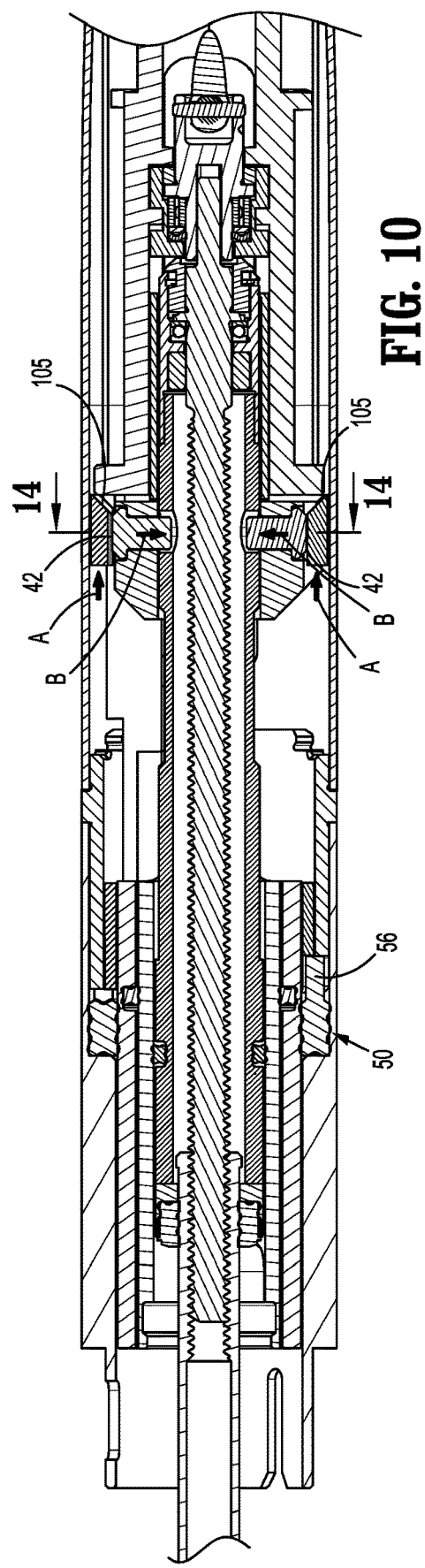
FIG. 10 is a side cross-sectional view of the distal portion of the tubular shaft and trocar assembly taken along section line 10-10 of FIG. 9.
Figure 11:
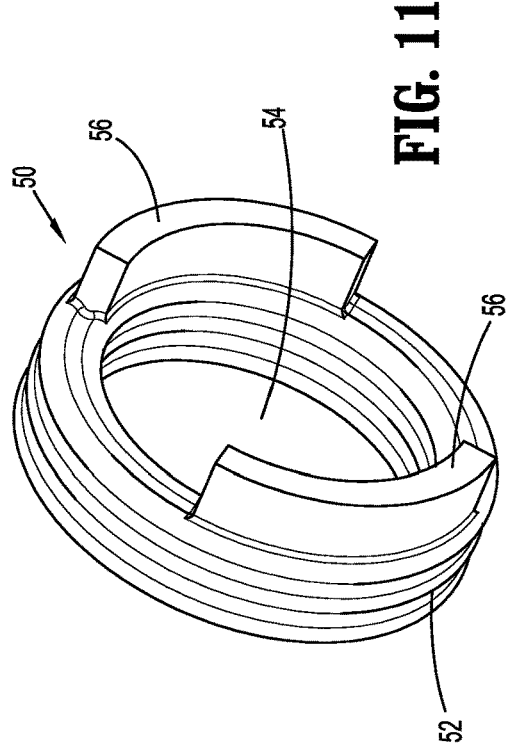
FIG. 11 is a perspective view of a seal.

As seen in FIG. 10, the trocar assembly 60 is retained in the tubular shaft 30 by the pins 40. The trocar assembly 60 is positioned coaxially within the lumen 34 of the tubular shaft 30 and slid distally into the lumen 34 until it is fully seated. The trocar assembly 60 is fully seated and rotated such that the orifices 66 of the sleeve 64 of the trocar assembly 60 are aligned with the receptacles 37 of the tubular shaft 30. Once the orifices 66 of the sleeve 64 of the trocar assembly 60 are aligned with the receptacles 37 of the tubular shaft 30, the support member 100 is slid proximally thereby camming the pins 40 towards the centerline of the tubular shaft 30, as indicated by arrows B, such that distal portions of the shanks 44 of the pins 40 are received in the orifices 66 of the sleeve 64 of the trocar assembly 60. This arrangement fixes the orientation and position of the trocar assembly 60 within the tubular shaft 30. A seal 50 is positioned at a distal end of the support member 100 for retaining the support member 100 in the second position that maintains the pins 40 inserted into the orifices 66 of the sleeve 64 of the trocar assembly 60. With additional reference to FIG. 11, the seal 50 has threading 52 on its distal end for engaging corresponding threads on an inner wall of the tubular shaft 30. This threaded arrangement maintains an axial position of the seal 50 once it is threadably coupled to the tubular shaft 30. The seal 50 has a central opening 54 with a diameter greater than an outer diameter of the trocar assembly 60. Additionally, the seal 50 has two distally extending tabs 56 that are diametrically opposed to one another. The tabs 56 are configured to engage a distal end of the support member 100 and retain the support member 100 in the second position.

Figure 12:
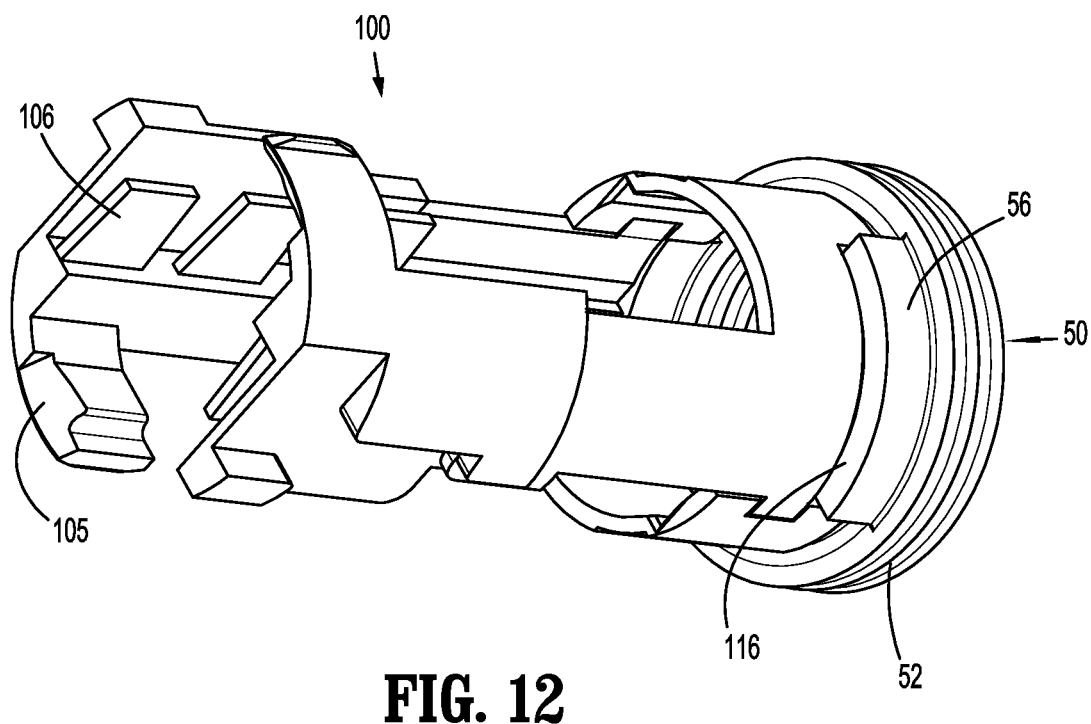
FIGS. 12 and 13 are perspective views of the seal of FIG. 11 coupled to the band support of FIG. 4.
Figure 13:
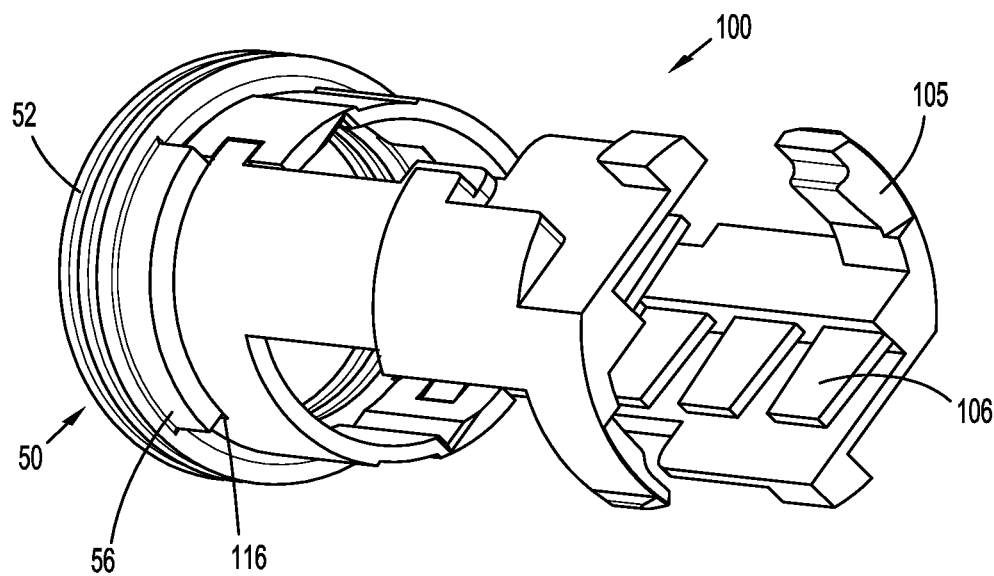

Referring now to FIGS. 12 and 13, the seal 50 is coupled to the support member 100. Specifically, the seal 50 is coupled to the distal end of the support member 100 such that the tabs 56 of the seal 50 are seated in notches 116 of the support member 100. As such, the seal 50 and the support member 100 are rotationally fixed with one another.

Figure 14:
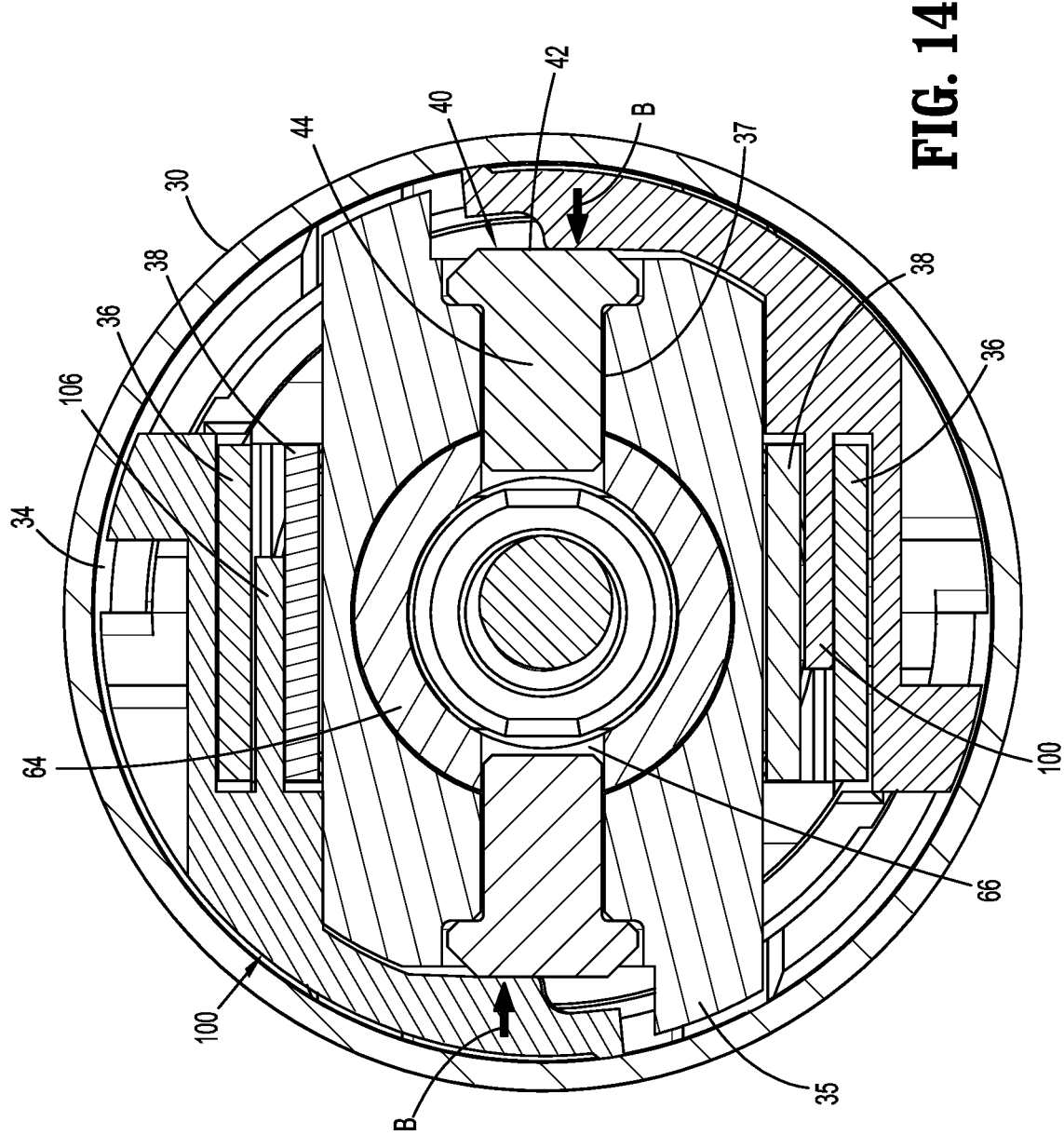
FIG. 14 is an end cross-sectional view of the distal portion of the tubular shaft and the trocar assembly of FIG. 10 taken along section line 14-14.

As seen in FIG. 14, the support member 100 is positioned within the lumen 34 of the tubular shaft 30 in its second (i.e., proximal) position. In the second position of the support member 100, the cam surfaces 105 of the support member 100 are in contact with the heads 42 of the pins 40. Contact between the cam surfaces 105 and the heads 42 of the pins 40 retains the pins 40 in an inserted position where distal ends of the shanks 44 of the pins 40 are located in the orifices 66 of the sleeve 64 of the trocar assembly 60. Locating the distal ends of the shanks 44 in the orifices 66 of the sleeve 64 of the trocar assembly 60 fixes the axial and radial position of the trocar assembly 60 with respect to the tubular shaft 30. An outer surface of the support member 100 is in contact with an inner wall of the tubular shaft 30 (i.e., an interference fit) which inhibits the pins 40 from sliding away from the centerline of the tubular shaft 30 (i.e., outboard) and maintaining them in the inserted position. Additionally, the projections 106 of the support member 100 are sandwiched between the knife band 38 and the staple band 36. Specifically, the knife band 38 is positioned between the projections 106 and a housing 35 while the staple band 36 is positioned between the projections 106 and an inner wall of the support member 100. This provides additionally support for the knife band 38 and the staple band 36 thereby minimizing any radial deflection by either the knife band 38 or the staple band 36 during an actuations sequence.

Persons skilled in the art will understand that the devices and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:

1. An end effector comprising:
   an elongate shaft having a lumen;
   an adapter disposed at a proximal end of the elongate shaft and configured to couple the elongate shaft with a handle assembly of a surgical instrument;
   a support member having proximal and distal openings defining a passage therethrough, the support member disposed in the lumen of the elongate shaft;
   a trocar assembly having a sleeve and a trocar member disposed therein, the trocar assembly insertable into the passage of the support member and the sleeve including an orifice extending through a wall thereof;
   a pin disposed in the elongate shaft, the pin slidable in a direction transverse to a longitudinal axis of the elongate shaft, the pin insertable into the orifice of the sleeve for retaining the trocar assembly longitudinally stationary relative to the elongate shaft and defining an inserted position of the pin; and
   a ramp located in a proximal region of the support member, the ramp engageable with a head of the pin to maintain the pin in the orifice of the sleeve.

2. The end effector according to claim 1, wherein the support member is slidable relative to the elongate shaft between a proximal position and a distal position.

3. The end effector according to claim 1, wherein the support member includes first and second portions that are attachable to each other.

4. The end effector according to claim 2, wherein the distal position of the support member relative to the elongate shaft allows movement of the pin between the inserted position and a retracted position.

5. The end effector according to claim 2, wherein the proximal position of the support member maintains the pin in the inserted position.

6. The end effector according to claim 1, wherein the support member further includes first and second pads that are configured to support first and second drive members to limit radial movement of the first and second drive members during an actuation sequence.

7. The end effector according to claim 2, further including a seal positioned at a distal end of the support member, the seal being threadably coupled to the elongate shaft to maintain the support member in the proximal position.

8. The end effector according to claim 2, wherein the ramp includes a tapered leading edge adapted to cammingly engage the head of the pin.

9. The end effector according to claim 4, wherein the trocar assembly is longitudinally repositionable relative to the elongate shaft with the pin in the retracted position.

10. An end effector for use with a surgical instrument, the end effector comprising:
    an elongate shaft having a lumen;
    an adapter disposed at a proximal end of the elongate shaft, the adapter configured for coupling the elongate shaft with a handle assembly of the surgical instrument;
    a support member having proximal and distal openings defining a passage therethrough, the support member disposed in the lumen of the elongate shaft and slidable relative to the elongate shaft between a proximal position and a distal position;
    a trocar assembly insertable into the passage of the support member, the trocar assembly having a trocar member extending from a sleeve, the sleeve including an orifice extending through a wall of the sleeve;
    a pin disposed in the elongate shaft, the pin slidable in a direction transverse to a longitudinal axis of the elongate shaft, the pin insertable into the orifice of the sleeve for retaining the trocar assembly longitudinally stationary relative to the elongate shaft and defining an inserted position of the pin; and
    a ramp having a tapered edge and located in a proximal region of the support member, the ramp engageable with a head of the pin to maintain the pin in the orifice of the sleeve.

11. The end effector according to claim 10, wherein the support member includes first and second portions that are attachable to each other.

12. The end effector according to claim 10, wherein the distal position of the support member relative to the elongate shaft allows movement of the pin between the inserted position and a retracted position.

13. The end effector according to claim 10, wherein the proximal position of the support member maintains the pin in the inserted position.

14. The end effector according to claim 10, wherein the support member further includes first and second pads that are configured to support first and second drive members to limit radial movement of the first and second drive members during an actuation sequence.

15. The end effector according to claim 10, further including a seal positioned at a distal end of the support member, the seal being threadably coupled to the elongate shaft to maintain the support member in the proximal position.

16. The end effector according to claim 10, wherein the tapered edge is adapted to cammingly engage the head of the pin.

17. A method of coupling a trocar assembly to an end effector comprising:
- inserting a trocar assembly into a lumen of an elongate shaft, the elongate shaft having an adapter disposed at a proximal end thereof that is configured to couple the elongate shaft with a handle assembly of a surgical instrument;
- sliding a support member disposed in the lumen of the elongate shaft proximally thereby moving from the support member from a distal position towards a proximal position; and
- engaging a head of a pin disposed in the elongate shaft with a ramp located in a proximal region of the support member and urging the pin into engagement with an orifice of a sleeve of the trocar assembly thereby retaining the trocar assembly longitudinally stationary with respect to the elongate shaft.

18. The method according to claim 17, wherein sliding the support member includes the support member having first and second portions that are attachable to each other.

19. The method according to claim 17, wherein sliding the support member includes the support member having first and second pads that are configured to support first and second drive members to limit radial movement of the first and second drive members during an actuation sequence.

20. The method according to claim 17, wherein engaging the head of the pin includes engaging the head of the pin with a tapered edge of the ramp.

* * * * *